US012599612B2

(12) United States Patent
Schmidt

(10) Patent No.: US 12,599,612 B2
(45) Date of Patent: Apr. 14, 2026

(54) PHARMACEUTICAL USE

(71) Applicant: Lucolas-M.D. Ltd., Birmingham (GB)

(72) Inventor: Alfred Schmidt, Nambsheim (FR)

(73) Assignee: Lucolas-M.D. Ltd., Birmingham (GB)

( * ) Notice: Subject to any disclaimer, the term of this patent is extended or adjusted under 35 U.S.C. 154(b) by 952 days.

(21) Appl. No.: 17/348,219

(22) Filed: Jun. 15, 2021

(65) Prior Publication Data

US 2021/0308148 A1 Oct. 7, 2021

Related U.S. Application Data

(63) Continuation of application No. 13/982,162, filed as application No. PCT/EP2012/051423 on Jan. 30, 2012, now abandoned.

(Continued)

(30) Foreign Application Priority Data

Jan. 31, 2011 (DE) ........................ 10 2011003 407.2

(51) Int. Cl.
    *A61K 31/5685* (2006.01)
    *A61K 31/353* (2006.01)
    (Continued)

(52) U.S. Cl.
    CPC ........ *A61K 31/5685* (2013.01); *A61K 31/353* (2013.01); *A61K 31/381* (2013.01);
    (Continued)

(58) Field of Classification Search
    CPC .............. A61K 31/5685; A61K 31/352; A61K 31/353; A61K 31/381; A61K 31/385;
    (Continued)

(56) References Cited

U.S. PATENT DOCUMENTS

| 6,147,054 A | 11/2000 | De Paoli Ambrosi et al. |
| 2002/0022052 A1 | 2/2002 | Dransfield |

(Continued)

FOREIGN PATENT DOCUMENTS

| CA | 2324077 A1 | 9/1999 |
| DE | 100 54 294 | 5/2002 |

(Continued)

OTHER PUBLICATIONS

Becker et al., Final Report of the Safety Assessment of Hyaluronic Acid, Potassium Hyaluronate, and Sodium Hyaluronate, 2009, International Journal of Toxicology, 28, 5-67 (Year: 2009).*

(Continued)

*Primary Examiner* — Bethany P Barham
*Assistant Examiner* — Ayaan A Alam
(74) *Attorney, Agent, or Firm* — Troutman Pepper Locke LLP; Scott D. Wofsy

(57) ABSTRACT

The invention relates to the use of a pharmaceutical medication comprising an aromatase inhibitor, preferably a steroidal aromatase inactivator and an antioxidant as effective ingredients for the treatment of sex hormone-dependent diseases. Furthermore, the invention relates to a composition comprising an aromatase inhibitor/—inactivator and α-lipoic acid and/or extract of green tea containing polyphenols. The combination of an aromatase inhibitor and—inactivator and α-lipoic acid and/or extract of green tea containing polyphenols is particularly suitable for the treatment of sex hormone-dependent diseases as well as for the treatment of benign tumors such as e.g. lipomatoses as occurring in Madelung's disease.

14 Claims, 5 Drawing Sheets

Related U.S. Application Data

(60) Provisional application No. 61/437,757, filed on Jan. 31, 2011.

(51) Int. Cl.
| | |
|---|---|
| *A61K 31/381* | (2006.01) |
| *A61K 31/385* | (2006.01) |
| *A61K 31/558* | (2006.01) |
| *A61K 31/5585* | (2006.01) |
| *A61K 36/82* | (2006.01) |
| *A61K 45/06* | (2006.01) |

(52) U.S. Cl.
CPC .......... *A61K 31/385* (2013.01); *A61K 31/558* (2013.01); *A61K 31/5585* (2013.01); *A61K 36/82* (2013.01); *A61K 45/06* (2013.01)

(58) Field of Classification Search
CPC .. A61K 31/558; A61K 31/5585; A61K 36/82; A61K 45/06
See application file for complete search history.

(56) References Cited

U.S. PATENT DOCUMENTS

| | | |
|---|---|---|
| 2002/0086856 A1 | 7/2002 | Schmidt et al. |
| 2003/0072821 A1 | 4/2003 | Morre et al. |
| 2003/0118623 A1 | 6/2003 | de Paoli Ambrosi |
| 2004/0018991 A1 | 1/2004 | Schmidt et al. |
| 2004/0053900 A1 | 3/2004 | Masferrer |
| 2004/0082557 A1 | 4/2004 | Wajszczuk et al. |
| 2004/0176339 A1 | 9/2004 | Sherman et al. |
| 2004/0192598 A1 | 9/2004 | Kragie |
| 2005/0281886 A1 | 12/2005 | Cattaneo |
| 2006/0263395 A1 | 11/2006 | Brown et al. |
| 2007/0072941 A1 | 3/2007 | Aylor et al. |
| 2007/0122509 A1 | 5/2007 | Chomczynski |
| 2007/0190043 A1 | 8/2007 | Sych et al. |
| 2009/0028952 A1 | 1/2009 | Bartis et al. |
| 2009/0110674 A1 | 4/2009 | Loizou |
| 2009/0111784 A1 | 4/2009 | Teichmann |
| 2009/0215731 A1 | 8/2009 | Birrell |
| 2011/0092580 A1 | 4/2011 | Palepu |

FOREIGN PATENT DOCUMENTS

| | | | | |
|---|---|---|---|---|
| DE | 102008012988 A1 | 9/2009 | | |
| EP | 0640595 A1 | 3/1995 | | |
| EP | 1854465 A1 * | 11/2007 | ........... | A61K 31/568 |
| GB | 1056192 A | 1/1967 | | |
| JP | 2005-513166 A | 5/2005 | | |
| WO | 1997010808 A1 | 3/1997 | | |
| WO | 99/01118 | 1/1999 | | |
| WO | 1999001118 A2 | 1/1999 | | |
| WO | 0069467 A1 | 11/2000 | | |
| WO | 03/057211 A1 | 7/2003 | | |
| WO | 2005055947 A2 | 6/2005 | | |
| WO | 2008115413 A1 | 9/2008 | | |
| WO | 2009070818 A1 | 6/2009 | | |
| WO | 2009/108361 | 9/2009 | | |
| WO | 2009/131196 A1 | 10/2009 | | |

OTHER PUBLICATIONS

Lee et al., α-Lipoic acid reduces matrix metalloproteinase activity in MDA-MB-231 human breast cancer cells, 2010, Nutrition Research, 30, 403-409 (Year: 2010).*

Nordman et al., The aromatase inhibitors in early breast cancer: who, when, and why?, MJA, vol. 183, No. 1, Jul. 4, 2005, pp. 24-27.

Campos, "Aromatase Inhibitors for Breast Cancer in Postmenopausal Women", The Oncologist 2004;9:126-136.

Lake et al., "Aromatase Inhibitors in Breast Cancer: An Update", Cancer Control, Nov./Dec. 2002, vol. 9, No. 6, pp. 490-498.

Szatrowski et al., "Production of Large Amounts of Hydrogen Peroxide by Human Tumor Cells1", Cancer REsearch 51, 794-798, Feb. 1, 1991.

Yokomizo et al., "Cellular Levels of Thioredoxin Associated with Drug Sensitivity to Cisplatin, Mitomycin C, Doxorubicin, and Etoposide1", Cancer Research 55, 4293-4296, Oct. 1, 1995, pp. 4293-4296.

Ferlini et al., "Tamoxifen induces oxidative stress and apoptosis in oestrogen receptor-negative human cancer cell lines", Brisith Journal of Cancer (1999) 79(2), 257-263.

Trachootham et al., "Selective killing of oncogenically transformed cells trhough a ROS-mediated mechanism by β-phenylethyl isothiocyanate", Cancer Cell 10, 241-252, Sep. 2006, pp. 241-252.

Kelloff et al., "Cancer Epidemiology, Biomarkers & Prevention", Cancer Epidemiology, Biomarkers & Prevention, vol. 7, 65-78, Jan. 1998.

Labrie, "Drug INsight: breast cancer prevention and tissue-target hormone replacement therapy", Nature Clinical Practice Endocrinology & Metabolism, Aug. 2007, vol. 3, No. 8, pp. 584-593.

Santen et al., "History of Aromatase: Saga of an Important Biological Mediator and Therapeutic Target", Endocrine Reviews, Jun. 2009, 30(4): 343-375.

Thompson Jr., et al., "Utilization of Oxygen and reduced Nicotinamide Adenine Dinucleotide Phosphate by Human Placental Microsomes during Aromatization of Androstenedione", J. Biol. Chem. 1974, 249:5364-5372.

McLachlan, "Functional Toxicology: A New Approach to Detect Biologically Active Xenobiotics", Environmental Health Perspectives, vol. 101, No. 5, Oct. 1993, pp. 386-387.

Scalzo, "Measurement of Free Radical Scavenging Activity of Gallic Acid and Unusual antioxidants as Sugars and Hydroxyacids", EJEAFChe. 9 (8), 2010, pp. 1360-1371.

Yamaguchi et al., "HPLC Method for Evaluation of the Free Radical-scavenging Activity of Foods by Using 1,1-Diphenyl-2-picrylhydrazyl#", Biosci. Biotechnol. Biochem., 62(6), 1201-1204, 1998.

Brown et al., "Hyaluronic acid: a unique topical vehicle for the localized delivery of drugs to the skin", JEADV (2005) 19, 308-318.

Tyczynski et al., "ENCR Cancer Fact Sheets, Breast Cancer in Europe", european Network of Cancer Registries International Agency for Research on Cancer, vol. 2, Dec. 2002, pp. 1-4.

Satoh et al., "INhiition of aromatase activity by green tea extract catechins and their endocrinological effects of oral administration in rats", Food and Chemical Toxicology 40 (2002) 925-933.

Magalhaes et al., "Chlorhexidine and green tea extract reduce dentin erosion and abrasion in situ", Journal of Dentistry 37 (2009) 994-998.

International Search Report mailed Apr. 2, 2012, in corresponding PCT Application No. PCT/EP2012/051423.

Lee et al., "a-Lipoic acid reduces matrix metalloproteinase activity in MDA-MB-231 human breast cancer cells", Nutrition Research 30 (2010) 403-409.

Dozlo et al., "The natural antioxidant alpha-lipoic acid induces p27Kip1-dependent cell cycle arrest and apoptosis in MCF-7 human breast cancer cells", European Journal of Pharmacology 541 (2010) 29-34.

Paepke et al., Overview of neoadjuvant endocrine therapy for receptor positive breast cancer in post-menopausal women, Geburtshilfe und Frauenheilkunde, 64 (12), 2004, pp. 1290-1298.

Abstract and translation of relevant parts. Clinical and Research, 61(5), 1984, pp. 146-148.

Lambert and Elias, Archives of Biochemistry and Biophysics, 501(1), 2010, pp. 65-72, abstract science direct.

Y. Nishino et al. "Antitumor Effect of a Specific Aromatase Inhibitor, 1-Methyl-Androsta-1,4-Diene-3,17-Dione (Atamestane), in Female Rats Bearing DMBA-Induced Mammary Tumors," J. Steroid Biochem, vol. 34, Nos. 1-6, pp. 435-437 (1989).

A. M. H. Brodie et al. "Effects of Aromatase Inhibitor 4-Hydroxyandrostenedione and Other Compounds in the 7,12-Dimethylbenz(a)anthracene-induced Breast Carcinoma Model," Cancer Research (Suppl.)42, 3360s-3364s, (1962).

(56)        References Cited

OTHER PUBLICATIONS

M. Kohler et al.,"Metabolism of 4-hydroxyandrostenedione and 4-hydroxytestosterone: Mass spectrometric identification of urinary metabolites," Steroids 72, 278-286, (2007).

Di Salle et al. Exemestance (FCE 24304) A new Steroidal Aromatase Inhibitor; J Steroid Biochem Mol Biol. Sep. 1992: 43 (1-3): 137-43.

Gedlicka et al. Amelioration of Docetaxel/Cisplatin Induced Polyneuropathy by a a-Lipoic Acid; Annals of Oncology 14: 339-340, 2003.

Pharmacia & Upjohn Co., Pfizer Inc., Approved Labeling for Aromasin®, 2005, pp. 1-29.

Balunas et al., Natural Products as Aromatase Inhibitors; Anticancer Agents Med Chem. Aug. 2008; 8(6); pp. 646-682.

* cited by examiner

PRIOR ART

PHARMACEUTICAL USE

This application is a Continuation of U.S. patent application Ser. No. 13/982,162, filed Jul. 26, 2013, which application is the national phase under 35 U.S.C. § 371 of PCT International Application No. PCT/EP2012/051423 which has an International filing date of Jan. 30, 2012, which claims priority to German Patent Application No. 10 2011 003 407.2, filed Jan. 31, 2011 and U.S. Provisional Application No. 61/437,757, filed Jan. 31, 2011. The contents of these applications are incorporated herein by reference in their entirety.

The invention concerns a medication and a pharmaceutical composition for the treatment of sex hormone-dependent diseases, in particular of breast cancer.

Sex hormone-dependent diseases have a high prevalence in the population. Breast cancer, for example, is the most frequently diagnosed cancer disease in women in Europe. 350,000 new cases are expected every year, while in the same period 130,000 women die of breast cancer (INCR Cancer Fact Sheets, Vol. 2, December 2002). Thus, 26.5% of all cancer diseases are breast cancer; 17.5% of all death caused by cancer, are caused by breast cancer. The therapy in the individual case depends on the staging of the tumor, for example, according to the stadium of the disease the biology of the tumor such as the expression of hormone receptors by the tumor cells. The expression of estrogen receptors (ER) or progesterone receptors (PR) allows for a medicinal therapy (e.g. as adjuvant therapy after mastectomy) with the estrogen antagonist Tamoxifen (Early Breast Cancer Trialists' Collaborative Group. N Engl J Med 1988; 319:1681-1692).

A further therapeutic approach, which is followed specially with women after menopause, is the targeted inhibition of aromatase. The enzyme aromatase catalyzes the conversion of androgens to estrogens. Postmenopausally, this reaction takes place mainly in the peripheral tissues, where the estrogen synthesized there exerts its effects locally, i.e. in the cell. This process can be described by the concept known as "Intracrinology" (Labrie F., Molecular and Cellular Endocrinology 1991; 78:C113-C118; as well as labrie F., Nature Clinical Practice Endocrinology & Metabolism 2007, Vol 3 No. 8; cf. also FIG. 3). Many studies provide evidence for the effectiveness of aromatase-inhibitors in breast cancer therapy in postmenopausal female patients with ER-positive tumors (review article: Nordman et al., MJA 2005; 183:24-27; Campos S M, The Oncologist 2004; 9:126-136; Lake D E and Hudis C, Cancer Control 2002; 9:490-498). Despite the successes, which have been reached in therapy by the use of aromatase inhibitors, the diagnosis breast cancer remains life-threatening and there remains to be a need for an improved breast cancer therapy.

Furthermore, besides breast cancer, there are other diseases, whose origin and course are sex hormone-dependent and for which therapy and prophylaxis effective and safe pharmaceuticals and uses thereof are needed.

It is an objective of the present invention to provide an effective therapeutic concept for the specific treatment of breast cancer and further to make the therapies of other hormone-dependent diseases possible. This objective is solved by the present invention.

The present invention concerns the use of a pharmaceutical medication, which contains an aromatase inhibitor and an antioxidant as active ingredient, and active component, respectively, for the treatment of sex hormone-dependent diseases.

Furthermore, in a particularly preferred embodiment, the invention concerns a composition, which contains a steroidal aromatase inactivator and $\alpha$-lipoic acid as antioxidant. The combination of an aromatase inhibitor and $\alpha$-lipoic acid is particularly suitable for the treatment of sex hormone-dependent diseases.

In the meaning of the invention a pharmaceutical medication is used for treatment or prophylaxis of breast cancer and sex hormone-dependent diseases in general. Therein, an aromatase inhibitor, preferably a steroidal aromatase inactivator, is combined with an antioxidant. In the combination the beneficial effects enhance each other significantly and in disproportionate manner. The therapeutic concept according to the invention provides that the aromatase inhibitor (aromatase inactivator) is particularly effective due to the concomitant use of an antioxidant. It is assumed that the antioxidant in the specific combination supports the prophylactic or therapeutic effectiveness of the aromatase inhibitors and that a synergistic interaction takes place. Antioxidants in the meaning of the present invention act as so-called radical scavengers in the organism, i.e. they deactivate highly-reactive radicals induced by exogeneous noxious agents (e.g. nicotine or alcohol), and endogeneously induced.

In the treatment of breast cancer the positive effect of the combination is apparently selective for cancer cells, thereby leading to reduced growth or regression of the tumor. It is assumed that the selectivity is connected to the special situation in cancer cells, where oxidative stress is generally increased (Szatrowski T P and Nathan C F, Cancer Res 1991, 51:794-798). The specific interaction and the mentioned synergistic effect, respectively, of the combination of an aromatase inhibitor with an antioxidant is all the more surprising in view of the existence of evidence that some chemotherapeutics exert their effects by increasing the oxidative stress in the cancer cell and thereby raise said stress above a critical limit and thus slow down or stop the tumor's proliferation (Yokomizo A. et al., Cancer Res 1995, 55:4293-4296; Ferlini C. et al., Br J Cancer 1999, 79:257-263; Trachootham et al., Cancer Cell 2006, 10:241-252). Accordingly, it could have been expected that the administration of an antioxidant together with a chemotherapeutic was not beneficial since the antioxidant would be supposed to reduce the oxidative stress.

In the context of the present invention, however, it has surprisingly been found that the combination of an antioxidant with an aromatase inhibitor in sex hormone-dependent diseases such as e.g. breast cancer, mastopathie, mastodynia or mastalgia, but also lipomes or lipomatoses such as, for example, Madelung's disease, has a significant effect, which becomes evident, for example, in the fact that breast tumors have regressed in very short time. This holds true also for the benign spread-out fat-tumors of large volume in Madelung's disease. It is assumed that in the case of benign tumors (similar to the situation of cancer cells, see above) the increased proliferation rate and the resulting increased (oxidative) metabolism form the basis for the unexpected effectiveness of the combination of aromatase inhibitors and antioxidants according to the invention.

Apparently, various cellular processes and interactions are influenced by both of the active ingredients contained in the medication in such a way that the combined use of an aromatase inhibitor on the one hand and an antioxidant on the other hand leads to a synergistic effect. The increased effectiveness of the active ingredients in combination allows for the use of the single active ingredients also in doses, which are below those of the respective monotherapies.

Thereby, undesired side-effects of, for example, the aromatase inhibitor, are reduced or avoided.

"Pharmaceutical medication" in the context of the present invention means that the active ingredients and active components, respectively, are administered, produced or provided in separate forms of application or dosage units, or as a combined composition, such as in a common application or dosage unit or in the form of a kit. In the meaning of the medication according to the invention, both active ingredients are administered and the medication is prepared, respectively, in such a way that their physiological effects are exerted simultaneously, in the same manner and at the same site, and that the time intervals overlap, respectively, during which the single active ingredients are physiologically effective. The surprising reciprocal enhancement of the active ingredients leads to an improved efficacy of the medication in the therapy and prophylaxis of sex hormone-dependent diseases in general and of cancer, mastopathie, mastodynia, mastalgia, lipomas or lipomatoses, in particular.

The invention shall be illustrated in detail by the following description of preferred embodiments and the Figures, without, however, limiting the general concept thereto.

-FIG. 1A shows mammographies, and FIG. 1B shows the evaluation of the radiological measurements of the tumor volume at the beginning of the treatment and 29 days later.

—FIG. 2A shows the mammographies, and FIG. 2B shows the analysis of the results of the radiological measurements of the tumor volume at the beginning of the treatment and 14 days later.

Due to the particular effect of the use of the medication according to the invention, its application can further be considered in the treatment or prophylaxis of tumors that grow in a hormone-dependent manner in general, breast cancer being merely one example. Because of the use of the antioxidant in the combination according to the invention, the invention is particularly useful in the prophylaxis and therapy of such diseases or conditions, in which a reduction of the number of free radicals in the organism, but, above all, also in the affected organ and tissue, respectively, has a positive effect. Due to the simultaneous additional use of an aromatase inhibitor, the use according to the invention is particularly effective in the case of sex hormone-dependent diseases.

Figure 3:
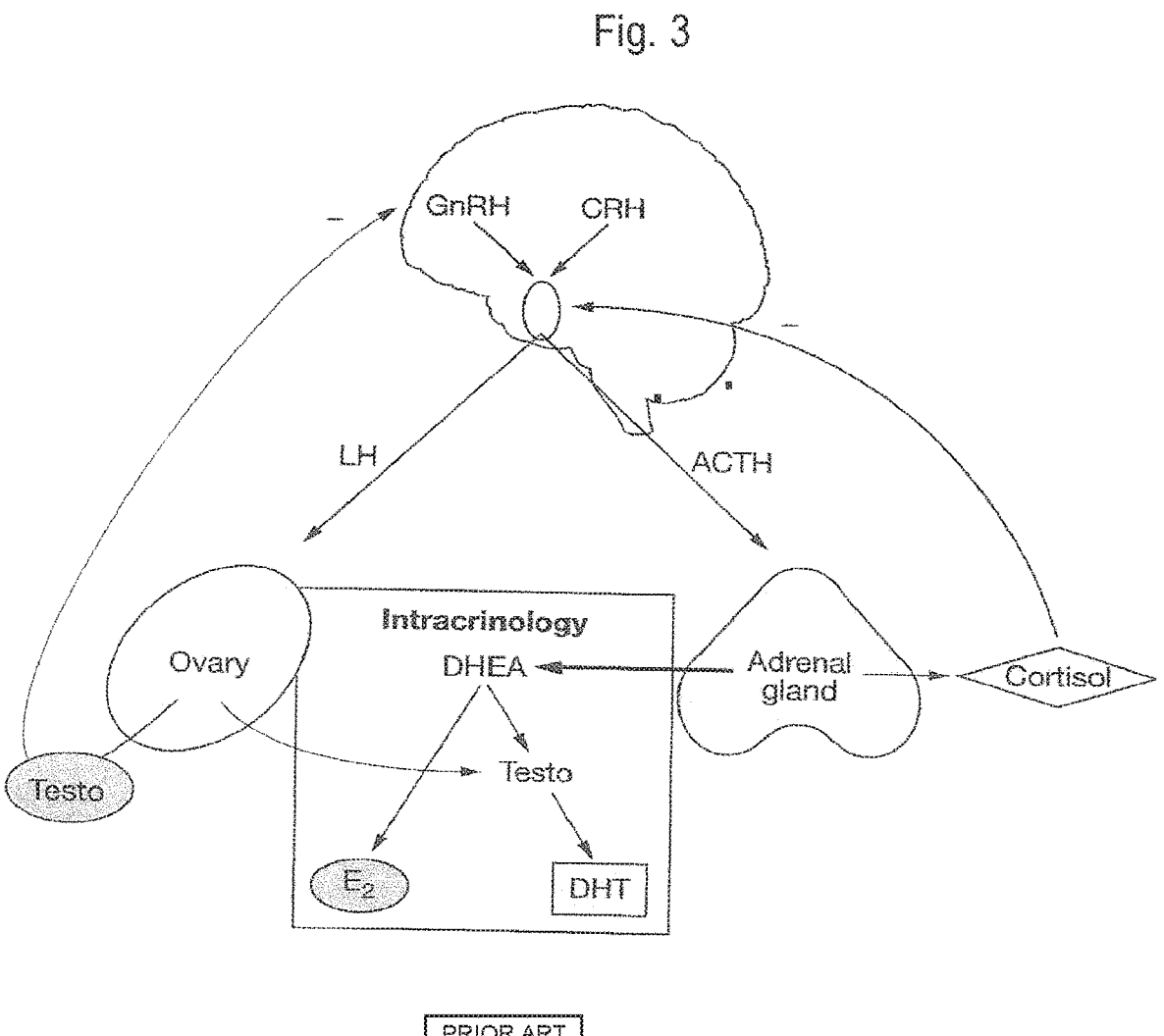
FIG. 3 shows the preferred concept according to the principle of "Intracrinology" and the corresponding preferred target of the inventive applications.

Sex hormone-dependent diseases in the meaning of the invention are any diseases and pathological conditions, which are generated by the effect of one or more sex hormones, caused by the imbalance of the local (extragonodal) production of sex hormones in the affected organs or affected tissue, or influenced in their progression. Relevant sex hormonal influencing factors and targets, in particular with regard to relevant steroidogenic enzymes in peripheral ("intracrine") tissue, that can be in connection with the therapy of sex hormone-dependent diseases according to the invention are clear from FIG. 3, which depicts a schematic representation of the role of ovarian and adrenaline sources of sex hormones, which are in particular typical for post-menopausal women, which however shall make clear herein the preferred embodiments of the present invention. Analogous to the situation after the menopause, estrogens and androgens are generated locally in the peripheral, "intracrine" target tissue (cf. lower part of FIG. 3). As far as small amounts of testosterone are generated locally and transported into the circulation system, an inhibitory effect (–) on the secretion in brain with regard to the gonadotropine-releasing hormone (GnRH) (cf. upper part of FIG. 3) takes place. On the other hand, adrenal glands release dehydroepiandrosterone (DHEA) as well as cortisol, which in turn reduces the secretion of the corticotropin-releasing hormone (CRH), which otherwise would stimulate the level of adrenocorticotropin (ACTH). In the specific peripheral target tissues, DHEA is converted to androgens and/or estrogens via the concept of "intracrinology". Only small amounts of these peripherally composed sex hormones reach the systemic circulation. Thus, the inventive application can indeed and very effectively take action in peripheral target tissue, and thus in particular take action locally, and above all via topical application.

In a preferred embodiment, the invention concerns the use of the medication for prophylaxis or therapy of breast cancer in female and in male patients. In combination with an anti-androgen therapy, such as 5-alpha-reductase inhibitors, LH-RH-analoga or androgen receptor blockers, also prostate hypertrophy and prostate cancer can be treated with particular success. Growth of the prostate is sex hormone-dependent in healthy individuals as well as in the special situation of prostate carcinoma. It is further known that the local hormonal balance, i.e. the interaction of estrogens and androgens, are of significant importance in the target tissue for prostate cancer (Kelloff et al., Cancer Epidemiology, Biomarkers and Prevention 1998; 7:65-78).

The use of an antioxidant in combination with an aromatase inhibitor is therapeutically particularly effective in diseases or conditions, whose origin or progression are influenced by estrogen or its precursors or derivatives. The positive effect of aromatase inhibitors has been demonstrated, in particular in tumors expressing estrogen receptor (ER-positive tumors) (review article: Labrie F., Nature Clinical Practice 2007; 3:584-593). It is assumed that the concomitant use of an aromatase inhibitor and of an antioxidant the synergism is achieved by the specific effect on different physiological processes.

Aromatase inhibitors in the meaning of the present invention are all substances, which—independently from their structure—are characterized by the common feature that they effectively inhibit or even inactivate aromatase (review article: Santen et al., Endocrine Reviews 2009; 30:343-375). The capacity of a substance to inhibit or inactivate aromatase, can be determined by methods, which are known to the skilled person. A radiometric essay, for example, allows for the measurement of aromatase activity in a single step by determining tritium-release from a tritium-labelled substrate (Thompson und Siiteri, Journal of Biological Chemistry 1974; 249:5364-5372).

The group of aromatase inhibitors is structurally heterogeneous and comprises steroidal as well as non-steroidal compounds, wherein representatives of both groups are relevant for the medication in the meaning of the invention. As non-steroidal aromatase inhibitors, e.g. Anastrazol, Letrozol und Vorozol can be used. Preferred steroidal aromatase-inhibitors (aromatase-inactivators) are 4-hydroxyandrostenedione, Exemestane, 4-acetoxyandrostenedione, 5-α-androst-3-ene-17-one and 3-α, 4-α-epoxy-5-α-androstane-17-one. Further examples of known aromatase-inhibitors are listed in pharmacopoeas such as the "Rote Liste".

An antioxidant according to the present invention is a "radical scavenger", which captures free radicals or terminates their harmful impact in the cell. According to the present invention, the administration of an antioxidant in combination with an aromatase-inhibitor apparently counteracts the origin and the proliferation of cancer, slows down the proliferation of a tumor or causes the reduction of the tumor mass, for example via apoptosis. These characteristics are of critical importance in the therapy and secondary prophylaxis as well as in the primary prophylaxis of breast/ prostate cancer. On the one hand, the primary origin of the tumor can be avoided if the mutagenic potential is decreased by reduction of the exogeneously (e.g. use of nicotine or alcohol) or endogeneously (e.g. via "waste products" or metabolites of estrogen metabolism) induced oxidative stress. On the other hand, further mutations frequently occur during the progression of an already existing tumor, which increase the aggressiveness of the tumor. Potentially, the formation of such further mutations and, thus, the progression of the tumor, can be avoided or slowed-down by the use of antioxidants. A synergy of an antioxidant and an aromatase-inhibitor in tumor therapy is mainly achieved also by the fact that the free radicals, which are also capable of imitating estrogen effects (McLachlan, Environmental Health Perspectives 1993; 101:386-387), are inactivated.

While the mode of action according to the invention is aligned and consistent as explained above, the group of antioxidants is structurally very heterogeneous. Suitable substances in the meaning of the invention are selected due to their capability to prevent the oxidation of other molecules. The skilled person is capable of identifying an antioxidant using established and published methods. The amount of free radicals can be measured, for example, by EPR (*Electric Paramagnetic Resonance*; Lo Scalzo, EJEAFChe 2010; 9:1360-1371). To this end, substances such as, for example, 5,5-dimethyl-1-pyrroline-N-oxide (DMPO) or 1,1-diphenyl-2-picrylhydrazyl (DPPH) are employed, which have a high affinity to free radicals and form stable compounds with them, that can be measured spectrometrically. Methods are also applied, in which the substance to be measured is purified chromatographically (e.g. by HLPC; Yamaguchi et al., Bioscience, Biotechnology, and Biochemistry 1998; 62:1201-1204). In the meaning of the invention antioxidative substances are administered. The administered antioxidants can be substances of various chemical classes and various origin. The antioxidative substances can also occur in the organism, their amount or availability, respectively, can effectively be increased, however, by the additional administration in the context of the medication of the invention, and/or eventually be provided at the desired target site by suitable application. Non-enzymatic antioxidants comprise, in particular, flavonoids (e.g. oligomeric proanthocyanidines (OPC), anthocyanes or polyphenoles such as quercetin or catechin); vitamins (e.g. vitamin C, vitamin E); carotenoides (e.g. beta-carotin, lycopen, lutein); minerals (e.g. copper, manganese, zinc, selenium); hormones (e.g. melatonin); steroids (e.g. cortisone); ubiquinones; N-acetylcystein; α-lipoic acid; an extract of green tea containing an antioxidative effective composition of polyphenols, optionally also amino acids, mineral nutrients (trace elements) and polysaccharides, and in particular which contains the specific highly antioxidative effective polyphenols epicatechin and epigallocatechin (e.g. OM24®, available from Omnimedica, Switzerland); and glutathion. Some enzymes fulfil the function of antioxidants and are termed enzymatic antioxidants, such as, for example, glutathionperoxidase, superoxide dismutase and katalase. In comparison with antioxidants that are probably only endogeneously occurring, or if so, are only accidentially or for different purposes added, according to the invention it can be made sure by adjusting suitable amounts that a certain desired therapeutic effect is achieved. This is preferably made sure in that the intentionally administered amount of antioxidant is at least 0.05, further preferred at least 0.1 wt.-% and in particular 0.5 wt.-% of the total composition, and/or that the antioxidant is administered locally in a targeted way at the desired treatment site, in particular locally-topically, or if so pulmonally or nasally.

In a particular embodiment the antioxidant, which is used together with an aromatase inhibitor, is α-lipoic acid (1,2-dithiolane-3-pentanoic acid) or green tea extract containing polyphenols, in particular OM24®. α-lipoic acid is active in the aqueous phases as well as in the lipid phases of cells.

The substance is excellently absorbed gastro-intestinally as well as via the skin. This allows for various possibilities of administration. α-lipoic acid is quickly converted to dihydrolipoic acid in the organism. Dihydrolipoic acid regenerates other, also endogeneous, antioxidants, such as vitamin C and vitamin E, which can lead to further enhanced effects, when α-lipoic acid is administered. α-lipoic acid furthermore induces the synthesis of glutathione in the tissue. Moreover, α-lipoic regenerates glutathione from glutathione disulfide.

In the meaning of the invention, the term "treatment" relates to the therapy as well as to the prophylaxis of sex hormone-dependent diseases and conditions. The inventive use of the medication is applied in the therapy and in the prophylaxis of cancer diseases and tumor diseases, respectively, in particular in the case of breast cancer. The use of aromatase inhibitors in combination with an antioxidant is particularly effective in the case of ER-positive tumors in post-menopausal female patients or in ER-positive tumors in male patients.

In a preferred embodiment, the aromatase inhibitor and the antioxidant are applied to the skin. This can be performed by using a combination preparation or by the simultaneous, or sequential but overlapping application of both active agents in the form of two separate dosage forms. Alternatively, both active agents can also be administered by different administration routes, as long as it is ensured that the aromatase inhibitor as well as the antioxidant exert their effects simultaneously and that the duration of effectiveness of one substance overlaps with that of the other substance, respectively.

In the case of the preferred (local) topical application to the skin, an active agent or both active agents are applied to the tissue to be treated and onto the skin area surrounding the tissue to be treated, respectively, in suitable carriers (e.g. creams, ointments, etc.). Thereby, the active agent or the active agents directly reach the target cells of the tissue to be treated, i.e. without systemic indirection and without liver passage (First Pass Effect). The active agent amount and the intervals of application are selected in such a manner that preferably no systemic plasma levels, but only locally active concentrations are reached. This has the advantage that besides the direct, immediate effect, side effects of the systemic administration of the active ingredient can be reduced or avoided. Also in the case of longer treatment periods or long-term therapy (e.g. in the situation of prophylactic use), undesired side-effects can thus be avoided or limited.

In a particularly preferred embodiment for the topical therapy, the medication according to the invention comprises hyaluronic acid. Therein, hyaluronic acid improves the absorption of the active agent or its diffusion across the callused skin, respectively, while at the same time retaining the active agent in the hypoderm and in the fat tissue (depot) and allowing for the local efficacy and avoiding the systemic distribution of the active agent via the blood circle, respectively (Brown and Jones, JEADV 2005; 19:308-318).

If desired, however, also systemically effective plasma levels can be reached by transdermal application of respective doses. Therein, the amount ratios are dependent from the physicochemical properties of the active agents, the intervals of application and the formulations which are used. The skilled person is capable of adapting the use according to the invention to the respective therapeutic or prophylactic situation.

In a preferred embodiment, steroidal aromatase inactivators such as exemestane, 4-hydroxyandrostenedione or 4-acetoxyandrostenedione, preferably α-lipoic acid or green tea extract containing polyphenols, in particular OM24®, are administered via the skin together with an antioxidant. Due to their lipophilic properties, steroidal aromatase inactivators are particularly well absorbed and reach the target tissue, such as the female breast and the tumor tissue, via skin layers that are rich in fat. This applies in particular manner to the case of the further combination with hyaluronic acid.

Alternatively, the active agents can be administered orally, parenterally (intravenously or intravascularly), pulmonally (inhalation), transnasally or rectally.

The medication according to the invention is preferably applied in the adjuvant and in the neoadjuvant therapy of breast cancer.

In a further embodiment, the medication is used for prophylaxis of breast cancer.

In primary prophylaxis women having a high risk to develop breast cancer are treated, preferably using the following dosages: once per day 0.5-2 g onto each breast: 0.05-5 weight-%, preferably 0.1-1 weight-%, e.g. 0.5 weight-% α-lipoic acid and 0.1-5 weight-%, preferably 0.5-2 weight-%, e.g. 1 weight-% acetoxyandrostenedione, which are integrated into a suitable basic cream, e.g. DAC basic cream having a composition, in which 100 g DAC contain: 0.5-10 g, preferably 2-7 g, e.g. 4.0 g glycerol monostearate; 0.5-10 g, preferably 3-8 g, e.g. 6.0 g cetyl alcohol; 1-15 g, preferably 3-10 g, e.g. 7.5 g medium chain triglycerides (e.g. neutral oil, miglyol); 10-40 g, preferably 20-30 g, e.g. 25.5 g white petroleum jelly; 0.5-10 g, preferably 3-8 g, e.g. 7.0 g MACROGOL®-20-glycerolmonostearate (polyethylene glycol-20-glycerolmonostearate); 2-25 g, preferably 8-15 g, e.g. 10.0 g propylene glycol; 10-80 g, preferably 30-60 g, e.g. 40.0 g purified water).

In the case of women that have already developed breast cancer, a secondary prophylaxis (adjuvant therapy) is performed after surgical therapy. In addition, in the case of one diseased breast, the contra-lateral breast is co-treated prophylactically, e.g. applying the following therapy schedule: twice per day (morning and evening) 0.5-4 g each on every breast: 0.05-5 weight-%, preferably 0.1-1 weight-%, e.g. 0.5% α-lipoic acid and 0.1 to 5 weight-%, preferably 0.5-2.5 weight-%, e.g. 1.5% acetoxyandrostenedione integrated in a basic cream (e.g. DAC).

In a preferred embodiment, the aromatase inactivator 4-hydroxyandrostenedione is used together with α-lipoic acid, in particular in the neoadjuvant therapy of ER-positive breast cancer. Therein, the active agents are applied topically to the breast either together or separately from each other. The concentrations of α-lipoic acid are preferably in a range from 0.5 weight-% to 2 weight %. The concentrations of the steroidal aromatase inactivator are preferably in a range of 1 weight-% to 3 weight-%. Furthermore, the dosage regime is preferably identical to the therapy regime in the secondary prophylaxis (adjuvant therapy). Exemplary dosage regimes are:

1) In primary prophylaxis, once per day 0.5-2 g of the topical dosage form onto each breast, preferably 0.5 weight-% α-lipoic acid, 1 weight-% acetoxyandrostenedione.

2) In neoadjuvant therapy, twice per day 2-4 g of the topical dosage form onto each breast in the concentration 1 weight-% α-lipoic acid and 2 weight-% acetoxyandrostenedione.

3) In secondary prophylaxis (adjuvant therapy) twice per day 4 g onto each breast in the concentration 0.5 weight-% α-lipoic acid and 1.5 weight-% acetoxyandrostenedione. The duration of the neoadjuvant therapy depends on the size of the primary tumor and the intentions of the surgeon. Since the effect of the therapy is visible and measurable already after two weeks, the therapeutic goal can be defined in a relatively precise manner. Normally, however, the neoadjuvant therapy should not be carried out for more than about three months before the surgical intervention. The efficacy and compatibility of the composition according to the invention are so convincing that elder patients can be treated solely by topical therapy. A surgical intervention poses a risk particularly in old age.

Moreover, the invention relates to a pharmaceutical composition comprising an aromatase inhibitor and specifically α-lipoic acid. The composition is a combination preparation, by which use the special technical effects as laid out above are obtained. The effect of the aromatase inhibitor and the effect of α-lipoic acid therein are synergistic as already described above.

Figure 1A:
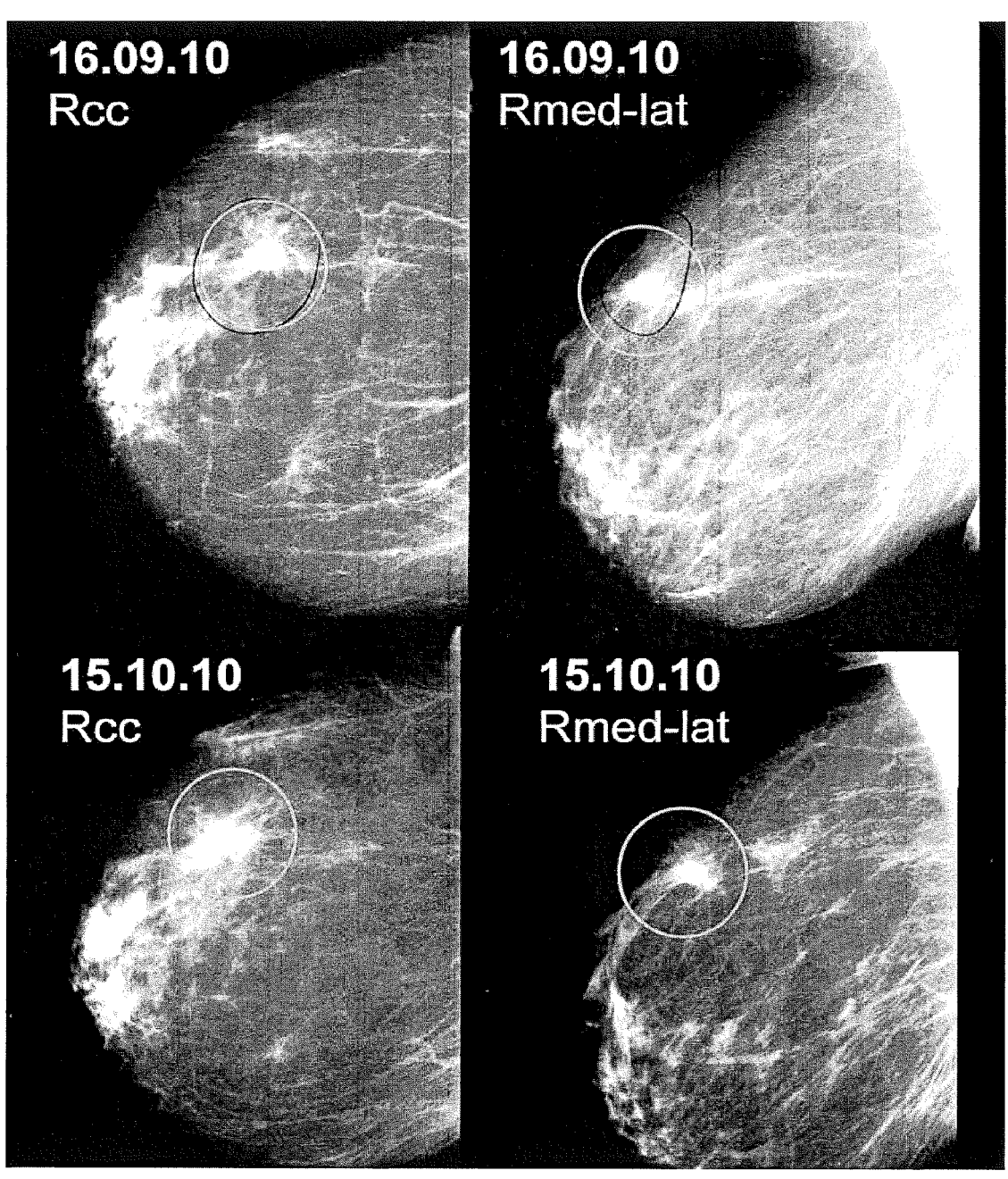
FIGS. 1A and 1B show the result of the treatment of a female patient with an ER-positive tumor in the right breast with the combination according to the invention
Figure 1B:
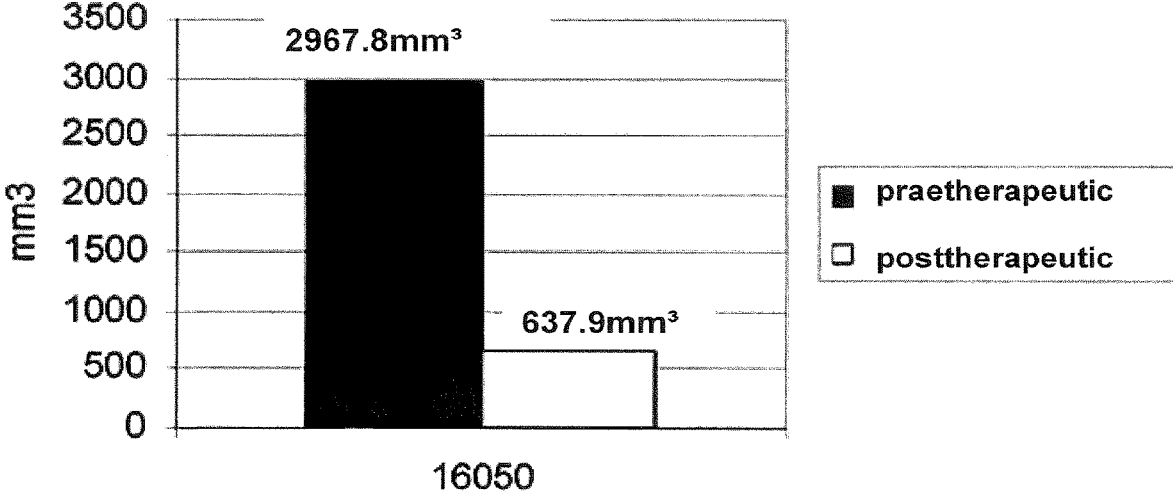
Figure 2A:
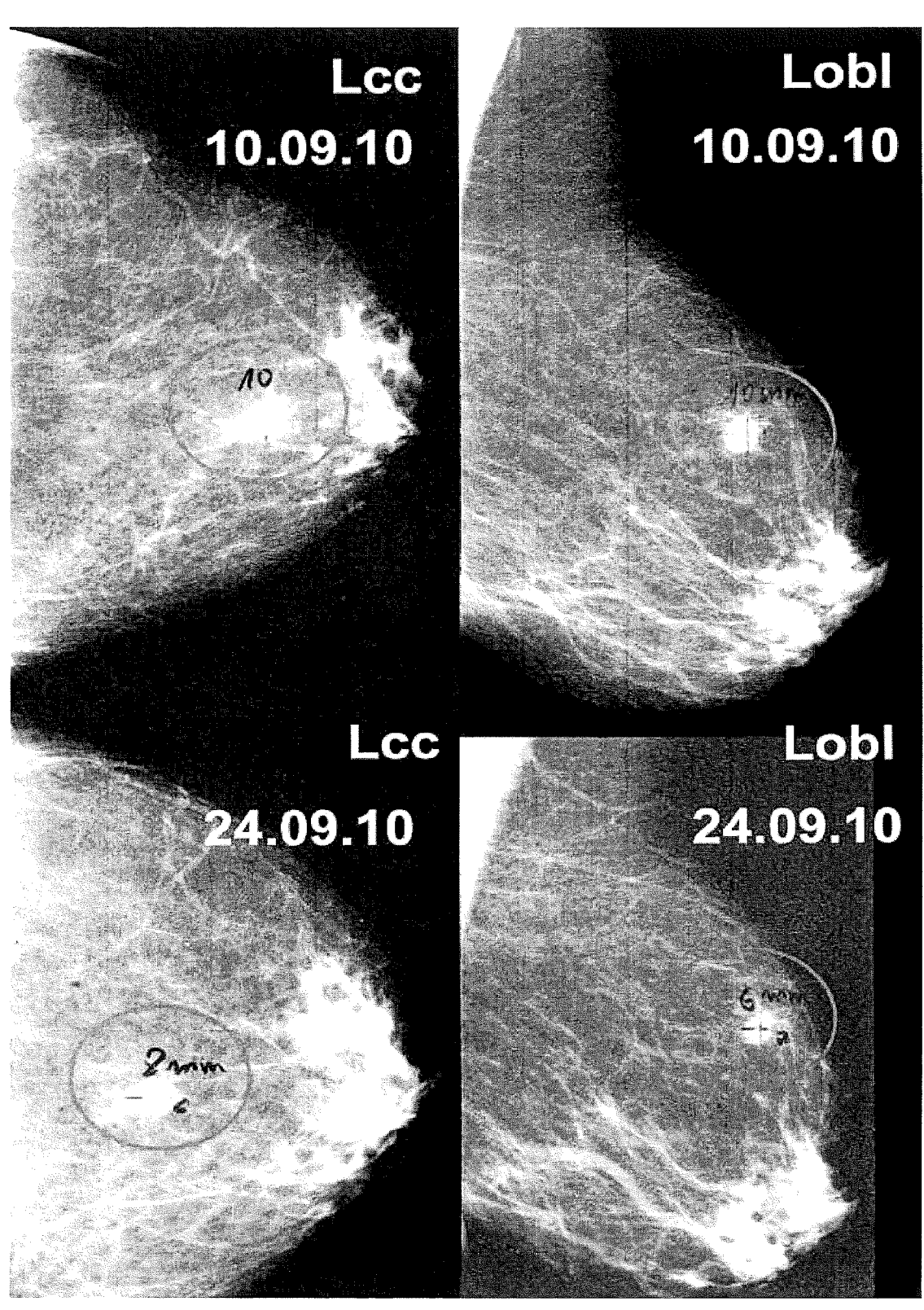
FIGS. 2A and 2B show shows the result of the treatment of a further female patient with an ER-positive tumor in the left breast
Figure 2B:
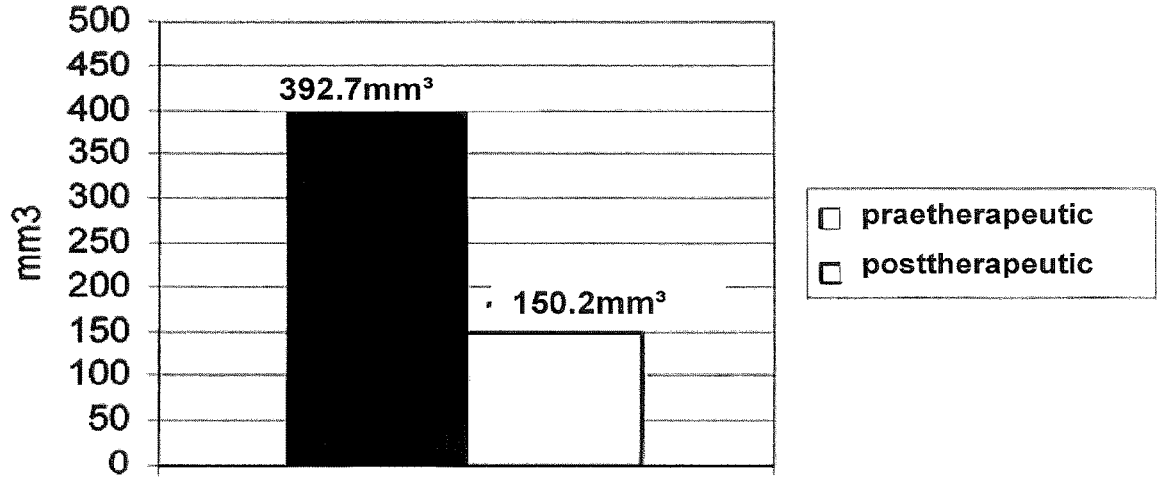

FIGS. 1 and 2 show the results of the treatment of two female patients with ER-positive tumors of the breast. In the case of one patient, a reduction of the tumor volume by 78.5% has been measured after 29 treatment days (FIG. 1A, 1B), in the case of another patient, a reduction of the tumor volume by 61.8% has been achieved after 14 days of treatment (FIG. 2A, 2B).

According to the present invention, a pharmaceutical medication comprising an aromatase inhibitor or aromatase inactivator and an antioxidant is used for the treatment of hormone-dependent diseases. As already laid out above, breast cancer is one of the diseases in which the medication is used. Moreover, the medication can further be used for the treatment of mastopathy, mastodynia and for probation in mastalgia.

Mastopathy is a benign change of the mammary gland of the breast. It occurs at least in each second woman and thus is the most frequent disease of the mammary gland of the woman. The affected women are in most cases 35 to 50 years; a mastopathy in women being younger than 25 years or being menopausal occurs very rarely.

Depending on the change of the mammary gland of the breast, different forms of mastopathy can be distinguished:

Fibrous mastophathy (Mastopathia fibrosa): In this type, glass-like connective tissue increasingly substitutes the fine layer of tissue that lines the inside of glandular ducts (epithel).

Fibrocystic mastopathy (Mastopathia fibrosa cystica): This type is characterized by an augmentation of the connective tissue and expansion of the glandular ducts.

Fibroadenomatic mastopathy (Mastopathia fibroadenomatosa): Typical for this type is a tumorous augmentation of mammary tissue cells (so-called adenomatous hyperplasy) in the glandular ducts, which can be filled with blood, pus or exudate.

Furthermore, in case of mastopathy, a classification in three groups takes place, which definition respectively depends on the severity of the change of the tissue of the mammary gland. By characterizing the severity, the risk for breast cancer of the affected women can be estimated. In mastopathy, in the first instance, the therapy aims at alleviating the symptoms developed from the changes of the tissue of the mammary gland. As an imbalance in the hormonal balance is responsible for mastopathy, up to now the treatment essentially aimes at balancing the excess of estrogen via gestagen. Probably, prolactin-inhibitors are effective in treating tension states and cystic changes of the breast occurring during a mastopathy. If the mastopathy causes severe symptoms, additionally Danazol, which inhibits the release of estrogen, can be administered for therapy.

In very rare cases of mastopathy it can also be necessary to remove the breast. This therapy is considered in particular in case of women being very afraid of breast cancer and in which multiple risk factors for degeneration of mastopathy coincide. These include a mastopathy grade III which is multiply secured by removal of tissue, a poor mammographical controlling of mastopathy, and cases of breast cancer in the family. These risk factors are of particular importance, if the mastopathy develops before the age of 40. Example 6 shows the "disappearance" of a fibrocystic mastopathy in a 49 year old woman after an about 12-month treatment with the medication according to the invention.

Mastodynia and mastalgia are amongst the so-called functional disturbances of the breast. Both terms are used frequently in the technical language for the discrimination between cycle-dependent (ca. 80%) and cycle-independent (ca. 20%) pain. In this context, mastodynia represents cycle- and hormone (estrogen)-dependent pain, mastalgia cycle-independent pain, which is rarely hormone-dependent. In mastodynia, the symptoms are cycle-dependent and occur in the period before and during menstruation. Pain, hypersensitivity for tactile stimuli, dragging pain, swellings with a feeling of tightness, a feeling of heaviness in and at both breasts, palpable hardenings (pre-menstrually) are by far the most frequent conditions, often beginning already two weeks before the menstruation. These conditions accompany many women during the entire pre-menopausal stage of their lives. Often, these women suffer from a significant increase of these ailments, starting from an age of 29 years.

About 80% of all female patients with breast pain suffer from cyclic breast pain. 30% of the female patients with mastodynia have a considerably compromised quality of life, also because of fear and stress resulting from the knowledge of having to live with the pain, which returns month after month.

Besides general measures, such as a well-fitted bra, a diet low in fat and the suggestion to eat plenty of vegetable food, a therapy with pharmaceutic substances is indicated in at least 30% of the female patients with severe symptoms. Besides the local application of progesterone (and diclofenac) gel, a systemic application of the estrogen antagonist Tamoxifen, the testosterone derivative Danazol, the administration of Bromocriptin (a dopamine agonist/ prolactine secretion inhibitor) is prescribed. The side-effects of these thereapies are in part substantial. A further field of application of the invention are benign tumors, which grow in a sex hormone-dependent manner and are caused by a local increase of fatty tissue. Estrogen enhances the increase of fatty tissue. The newly synthesized fat increases the body's own production of estrogen and free radicals by fat cells. Presumably, the activity of the enzyme aromatase increases in the fat cells, thus increasing the activity of converting testosterone to estrogen and the generation of free radicals. In addition, also the number of receptors, at which estrogen and free radicals can become effective, increases in the cells. This, on the other hand, leads to an enhanced effect of the estrogens and free radicals. A fatty tissue immanent autonomous vicious circle-situation, which is effectively counteracted by the medication according to the invention.

Thus, with the help of the inventive indication, it could be shown for the first time that the lipoma (benign tumor of the cells of the fatty tissue) and the lipomatosis are benign fatty tumors which proliferate in a sex hormone-dependent manner. Lipomatosis is a diffuse increase of fatty tissue at distinct sites of the body—in the majority of cases starting from the subcutaneous fat tissue—, e.g. the neck, the upper trunk (e.g. back) or the hips, or also all in combination or together can be affected. As synonyms for lipomatosis are used amongst others:

symmetric adenolipomatosis;
Lipomatosis *symmetrica;*
diffuse symmetric lipomatosis;
generalized symmetric lipomatosis;
multiple symmetric lipomatosis;
localized symmetric lipomatosis;
Lipomatosis simplex indolens;
Launois-Bensaude-Syndrom;
Madelung's disease.

There is no causal therapy either for lipomas or for any form of lipomatosis. Surgical reduction or liposuction are basically possible, however, not without risks and linked to a high recurrence rates. By the present invention it could be shown for the first time that the fatty tissue, which, as described above, grows in a sex hormone-dependent manner, by combination of a radical scavenger (e.g. 0.5% α-lipoic acid) with an aromatase inhibitor (e.g. 1.5% 4-acetoxyandrostenedion) in combination with the release system of hyaluronic acid (e.g. 0.2%) not only slows down the proliferation of fat tumors, but leads to the "melting" of these. Example 8 shows this effect in the case of a 56 year old female patient with very severe Madelung's disease. Example 9 the shrinking of an egg-shaped lipoma of about 12 cm above the left shoulder joint of a 71 year old patient.

The present invention is further illustrated by the following examples, without being limited by the same.

Examples 1-5 illustrate the inventive use of the medication in the therapy of breast cancer

EXAMPLE 1

An ER-positive tumor has been diagnosed in the right breast of a 59-year-old female patient. Prior to the start of the treatment, the tumor has been measured mammographically (FIG. 1A). In the following 29 days, α-lipoic acid 0.5% and 4-hydroxyandrostenedione 1.5% (integrated in the basic cream DAC) have been administered topically onto each breast twice per day, 2 g each. Subsequently, the tumor has been measured again (FIG. 1A) and the tumor volume before and after the treatment has been shown graphically in a diagram (FIG. 1B). The tumor volume has been reduced by 78.5% over the course of the 29 days of treatment.

EXAMPLE 2

A 69-year-old female patient has been diagnosed with an ER-positive tumor in the left breast. A treatment of the breasts was carried out for 14 days by topical administration of α-lipoic acid 0.5% and 4-hydroxyandrostenedione 1.5% (integrated into the basic cream DAC) twice per day, 2 g each. The tumor volume has been determined before and after the treatment as described under Example 1 (FIG. 2A). The tumor volume after treatment was reduced by 61.8%.

EXAMPLE 3

An ER-positive tumor has been diagnosed in the right breast of a 53-year-old female patient. Prior to the start of the treatment, the tumor was measured mammographically. In the following 24 days α-lipoic acid 0.5% and 4-hydroxy-androstenedione 1.5% (integrated into the basic cream DAC) have been administered topically onto each breast twice per day, 2 g each. Subsequently, the tumor has been measured again and the tumor volume has been compared. The tumor volume has been reduced by 76% over the course of the 24 days of treatment.

EXAMPLE 4

An ER-positive tumor has been diagnosed in the left breast of a 62-year-old female patient. A treatment was carried out by topical application using the composition according to the invention. In the following 14 days, α-lipoic acid 0.5% and 4-hydroxyandrostenedione 1.5% (integrated into the basic cream DAC) have been applied topically onto each breast twice per day, 2 g each. The tumor volume before and after the treatment has been determined as described under Example 1. The volume of the tumor has been reduced by 64.5% after the treatment.

EXAMPLE 5

A 47-year-old female patient suffered from an ER-positive tumor in the right breast. For 28 days treatment as described under Example 1 and 2 has been carried out and the tumor volume at the beginning and at the end of the treatment, respectively, has been determined. A reduction by 60.5% has been found.

EXAMPLE 6

Inventive use of the medication in mastopathy.
S.H.C., female, 49 years.
The following combination was selected for the use: As active ingredients
OM24® 0.4%
Exemistane 1.0%
As additive (facilitator of absorption and distribution) hyaluronic acid 0.3%.
Anamnesis and Therapy:
A fibrocystic mastopathy grade II has been diagnosed in the patient. At the request of the patient, in order to avoid the risk of breast cancer, a therapeutic trial has been carried out by using the above combination, once per day, 2 g onto each breast. The mastopathy (mastopathia fibrosa cystica) has been degenerated completely after 11 months of application.
The breast tissue exhibited an ordered structure without any micro-calcification.
Examples 7 and 8: Use of the medication according to the invention in mastodynia:
The following combination was selected for the use:
As active ingredients:
α-lipoic acid 0.5%,
4-acetoxyandrostenedione 1.0%, hyaluronic acid 0.2% (merely as a facilitator of absorption and distribution).

EXAMPLE 7

I.H., female, 21 years.
Anamnesis: Menstrual pain occurring monthly since age 13, becoming so strong during the preparation of High School exams (at age 18), that her gynaecologist carried out a mammography, which however merely revealed as a result a slight mastopathy in the upper quadrants. Previous prescription: Voltaren gel applied multiple times per day as needed.
Present situation: Pain occurring in both breasts 3-5 days prior to each menstruation together with a strong sensation of tension, from the upper quadrants in a seemingly bundled manner shooting towards the nipples. Further continuing under Voltaren gel, during the whole menstrual cycle, afterwards slowly decreasing pain, feeling of tension and dragging until about the $12^{th}$ day after beginning of the menstruation.
Individual Trial Application Using the Medication According to the Invention:
4 g once per day, namely 2 g applied onto each breast and massaged in with caution. The individual trial application started about 2 weeks before the beginning of the menstruation.
Result of the Individual Trial Application:
The next menstruation proceeded with significantly reduced tension pain in the breast. Overall symptoms: less limiting and ceasing faster. Already 5 days after the beginning of the menstruation the patient was free of any pain. Continuation of the trial application with daily application.
Result after the Second Following Menstruation: Absence of Pain
Continuation of the trial with the medication according to the invention without any undesired side effects.

EXAMPLE 8

S.P., female, 32 years, married;
Anamnesis: Pre-menstrual syndrome with symptoms of strong pain in both breasts since puberty. Dynamic increase of the symptoms since age 27 with extremely strong tactile sensitivity, strong sensation of swelling and tension with pain symptoms diffusely radiating into the chest and the arms, which becomes virtually unbearable until the beginning of the menstruation. Unable to work because of these conditions for 2-4 days per month since 3 years. Intimate touching not possible for 14 days per month due to the pathologic tactile hyper-sensitivity. Fading-away of the symptoms only 7-10 days after the beginning of the menstruation.
Mammography 6 months ago without finding. Writing a pain-diary since 1 year in order to document the premenstrual syndrome.
Previous prescription: Testosterone gel and/or Voltaren gel for years basically without any effect.
The same applies to temporary therapeutic attempts with Bromocriptin or Danazol. Only administration of Tamoxifen 20 mg led to a considerable alleviation of the symptoms, leading, however, to equally substantial side-effects, mainly in the cardiovascular field (uncontrolled increase of blood pressure). This led to quitting the therapy and already after two menstruation cycles the symptoms showed again their original intensity.

Individual trial application with the medication according to the invention: 4 g, twice per day (in the mornings and in the evenings), namely 2 g applied onto each breast and massaged in cautiously. The trial application started 2 weeks prior to the beginning of the menstruation.

Result of the Trial Application:

The next menstruation proceeded with considerably reduced tension pain in the breast. Overall symptoms develop in a less limiting way and cease faster. Already 5 days after the beginning of the menstruation, the patient was free of any pain.

Continuation of the Trial with Daily Application:

Subsequent period: considerably reduced symptoms of swelling and tension, noticeably reduced pain symptoms, mainly in the breasts, less radiating, no incapacity to work.

Continuation of the Trial Application:

3. menstruation: further decrease of the sensation of swelling and tension, reduced pain, remaining only in the breasts, substantially reduced tactile sensitivity, no incapacity to work.

Further periods of application: almost no remaining sensations of swelling and tension, almost no remaining tactile sensitivity, practically free of pain, no incapacity to work due to mastodynia. No undesired side-effects during the whole treatment period.

Examples 9 and 10: Use of the medication according to the invention in benign tumors (fat tumors).

For this application, the following combination was selected: as active ingredients α-lipoic acid 1.0%, 4-hydroxyandrostenedione 1.5%, hyaluronic acid 0.2% (as a local delivery system) integrated into a basic cream (DAC).

EXAMPLE 9

Patient: E.M.S., 56 years, female: the patient suffers from a very rare, extreme disorder in fat distribution (incidence: 1:25.000 in men and 1:300.000 in women) caused by a Madelung's diseases since almost 15 years, which has led, on the one hand, to a grotesque redistribution of fatty tissue with substantial shrinkage of the breasts and the posterior and to a symmetric lipomatosis focussed on the upper trunk and, on the other hand, to impaired motility due to the disturbing fat tumors. In addition, Ms. S. suffers from considerable pain in the fat tumors on the neck, on the back, at the throat, at the lateral thoracic wall, the sides above the shoulder and at the upper arms. This corresponds to the typical image of a Madelung's disease with Lipomatosis dolorosa. The patient had multiple surgeries carried out in cycles from the years 1995 to date. For the last series of surgeries (back and neck, each of those semi-laterally in separate surgeries, likewise upper arms and sides) in the year 2008, six appointments for surgery were required in total. Until December 2010: recurrence in all localizations; further increased growth of the spread-out fat tumors.

The grotesque transformation of the physical appearance and the considerable pain symptoms together with the difficulties in carrying adequate cloth, have led to a restriction of the life quality, which is difficult to tolerate. The situation is further aggravated by the fact that the patient avoids any intimate contact with her partner since years due to a sense of shame and due to the pain. The patient's condition at the beginning of the trial therapy with the medication according to the invention was worse than at the beginning of the last cycle of surgeries in the year 2008.

The patient naturally fears a new surgical intervention as obviously also in that case again multiple recurrences are to be expected.

Start of the individual trial cure on Dec. 14, 2010; the composition according to the invention is massaged into all the fat tumors twice per day. Weekly measurements are carried out of the following regions: neck, breast, left and right upper arms, hip and throat.

Result: not only could the excessive growth be stopped, but the following results have been achieved: during the course of a therapy, which lasted for 6 weeks so far, the circumferences decreased as follows:

neck from 36 cm to 31.5 cm,
breast from 116 cm to 111.5 cm,
upper arm left from 42 cm to 34 cm,
upper arm right from 36 cm to 33 cm,
hip from 104 cm to 101 cm,
throat circumference from 42 cm to 38.5 cm (see Table 1)

TABLE 1

| Results of the measurements in cm (Example 8) | | | | | | |
|---|---|---|---|---|---|---|
| DATE | NECK | BREAST | ARM le | ARM ri | HIP | THROAT CIRCUM- FERENCE |
| 14 Dec. 2010 | 36 | 116 | 42 | | | 42 |
| 21 Dec. 2010 | 35 | 114 | 37 | | 103 | 41 |
| 28 Dec. 2010 | 34 | 114 | 36 | 33 | 102 | 40 |
| 05 Jan. .2011 | 33 | 114 | 35 | 33 | 101 | 40 |
| 12 Jan. 2011 | 32 | 112 | 34 | 33 | 101 | 39 |
| 19 Jan. 2011 | 32 | 112 | 34 | 33 | 101 | 39 |
| 26 Jan. 2011 | 31.5 | 111.5 | 34 | 33 | 101 | 38.5 |

On average, the patient consumed about 100 g per week of the composition according to the invention, which means, in an application twice per day, a concentration of the active ingredients of 140 mg α-lipoic acid and
about 214 mg 4-hydroxyandrostenedione.

Under the present treatment no undesired effects whatsoever; the trial cure is continued.

EXAMPLE 10

The 71-year-old male patient E.H.S. over the course of 1 year developed a lipoma above the left shoulder joint, which in the beginning was of the size of a pigeon egg. Until the beginning of the trial cure with the composition according to the invention, the lipoma enlarged to an egg-shaped structure of about 12 cm longitudinal section, 8 cm latitudinal section, and 2.5 cm in height. Besides the cosmetic aspect, the lipoma influences the up-and-down movements of the left arm and the shoulder joint by causing pain, since the lipoma apparently triggers substantial pain during movement by exerting pressure on the supraspinal ligament in the shoulder joint. The patient was willing to undergo surgical treatment.

However, the patient now decided in October 2010 to use the composition according to the invention.

Application: twice per day about 2 g massaged into the entire region of the lipoma.

Result: after 10 weeks of treatment:

The lipoma shrank
in the longitudinal section from 12 cm to 7 cm,
in the latitudinal section from 8 cm to 4 cm,
in height from 2.5 cm to 1 cm.

The pain due to pressure and movement is considerably reduced, so that the left arm can again be moved almost freely.

As the application of the composition according to the invention is not only highly effective, but also mediates a pleasant skin sensation, the trial cure is continued.

Goal: complete dissolution of the lipoma.

What is claimed is:

1. A method for treating a sex-hormone dependent disease in a subject diagnosed with the sex-hormone dependent disease, wherein said sex-hormone disease is estrogen-receptor positive breast cancer, the method comprising topically administering to the subject a treatment effective amount of a pharmaceutical medication consisting essentially of two active ingredients, wherein the two active ingredients are a steroidal aromatase-inhibitor and an antioxidant that is different from the aromatase-inhibitor;

wherein the steroidal aromatase inhibitor is a steroidal aromatase inactivator selected from the group consisting of 4-hydroxyandrostenedione, exemestane, 4-acetoxyandrostenedione, 5-alpha-androst-3-ene-17-one, and 3-alpha,4-alpha-epoxy-5-alpha-androstane-17-one;

wherein the antioxidant is alpha-lipoic acid; and wherein the pharmaceutical medication comprises 0.05-5 wt.-% of antioxidant and 0.1-5 wt.-% steroidal aromatase inhibitor.

2. The method according to claim 1, wherein the treatment is effective only in a peripheral, intracrine target tissue.

3. The method of claim 1, wherein the pharmaceutical medication is a topical dosage form.

4. The method according to claim 1, wherein the treatment is an adjuvant or neoadjuvant therapy of breast cancer.

5. The method according to claim 1, wherein the amount of antioxidant is at least 0.05 wt.-%, at least 0.1 wt.-%, or at least 0.5 wt.-% of the total pharmaceutical medication.

6. The method according to claim 1, wherein the aromatase-inhibitor is exemestane or 4-hydroxyandrostenedione, and wherein the antioxidant is alpha-lipoic acid.

7. The method according to claim 1, wherein the treatment is continued or resumed after an initial treatment of breast cancer.

8. The method according to claim 7, wherein the treatment that is continued or resumed after initial treatment of the estrogen-receptor positive breast cancer comprises topical administration of 0.5-4 g of the pharmaceutical medication onto the diseased breast in a suitable base cream.

9. The method according to claim 1, wherein the subject is a woman.

10. The method according to claim 1, wherein the pharmaceutical medication further comprises hyaluronic acid.

11. A method for treating a sex-hormone dependent disease in a subject diagnosed with the sex-hormone-dependent disease, wherein said sex-hormone disease is estrogen-receptor positive breast cancer, the method comprising topically administering to the subject a treatment effective amount of a pharmaceutical composition, consisting of:

a steroidal aromatase-inactivator, wherein the steroidal aromatase-inactivator is 4-hydroxyandrostenedione, exemestane, or 4-acetoxyandrostenedione, wherein the steroidal aromatase-inactivator is from 1 wt. % to 3 wt. % of the total composition;

an antioxidant, wherein the antioxidant is α-lipoic acid, wherein the antioxidant is from 0.5 wt.-% to 2 wt. % of the total composition;

hyaluronic acid, wherein the hyaluronic acid is from 0.2 wt.-% to 0.3 wt. % of the total composition;

optionally, one or more carriers, wherein the one or more carriers are selected from the group consisting of glycerol monostearate, cetyl alcohol, medium chain triglycerides, white petrolatum, polyethylene glycol-20-glycerolmonostearate, propylene glycol, and purified water; and optionally, one or more additional additives selected from the group consisting of amino acids, mineral nutrients (trace elements) and polysaccharides;

wherein said topical pharmaceutical composition is formulated as a cream, a gel, an ointment or an emulsion.

12. The method according to claim 11, wherein the steroidal aromatase-inactivator, wherein the steroidal aromatase-inactivator is 4-hydroxyandrostenedione or exemestane, wherein the steroidal aromatase-inactivator is from 1 wt. % to 3 wt. % of the total composition;

the antioxidant is α-lipoic acid, wherein the antioxidant is from 0.5 wt.-% to 2 wt. % of the total composition;

hyaluronic acid, wherein the hyaluronic acid is from 0.2 wt.-% to 0.3 wt. % of the total composition;

glycerol monostearate, cetyl alcohol, medium chain triglycerides, white petrolatum, polyethylene glycol-20-glycerolmonostearate, propylene glycol, and purified water as carriers; and optionally, one or more additional additives selected from the group consisting of amino acids, mineral nutrients (trace elements) and polysaccharides.

13. The method according to claim 11, wherein the carrier is a combination of glycerol monostearate, cetyl alcohol, medium chain triglycerides, white petrolatum, polyethylene glycol-20-glycerolmonostearate, propylene glycol, and purified water.

14. A method for treating a sex-hormone dependent disease in a subject diagnosed with the sex-hormone dependent disease, wherein said sex-hormone dependent disease is estrogen-receptor positive breast cancer, the method comprising topically administering to the subject a treatment effective amount of a pharmaceutical medication consisting essentially of two active ingredients, wherein the two active ingredients are a steroidal aromatase-inhibitor and an antioxidant that is different from the aromatase-inhibitor;

wherein the steroidal aromatase inhibitor is a steroidal aromatase inactivator selected from the group consisting of 4-hydroxyandrostenedione, exemestane, 4-acetoxyandrostenedione, 5-alpha-androst-3-ene-17-one, and 3-alpha,4-alpha-epoxy-5-alpha-androstane-17-one;

wherein the antioxidant is alpha-lipoic acid;

wherein the pharmaceutical medication comprises 0.05-5 wt.-% of antioxidant and 0.1-5 wt.-% steroidal aromatase inhibitor; and wherein the treatment is continued or resumed after an initial treatment of breast cancer.

* * * * *